United States Patent [19]

Cachia

[11] Patent Number: 5,893,850

[45] Date of Patent: Apr. 13, 1999

[54] BONE FIXATION DEVICE

[76] Inventor: Victor V. Cachia, 28334 Paseo Michele, San Juan Capistrano, Calif. 92675

[21] Appl. No.: 08/745,652

[22] Filed: Nov. 12, 1996

[51] Int. Cl.[6] .................................................. A61B 17/58
[52] U.S. Cl. ............................ 606/72; 606/73; 606/63; 606/64; 606/65
[58] Field of Search .............................. 606/60, 61, 63, 606/64, 65, 72, 73

[56] References Cited

U.S. PATENT DOCUMENTS

| 2,077,804 | 4/1937 | Morrison . | |
|---|---|---|---|
| 2,485,531 | 10/1949 | Dzus et al. . | |
| 2,489,870 | 11/1949 | Dzus . | |
| 3,489,143 | 1/1970 | Halloran . | |
| 4,052,988 | 10/1977 | Doddi et al. . | |
| 4,275,717 | 6/1981 | Bolesky | 128/92 |
| 4,688,561 | 8/1987 | Reese . | |
| 4,790,304 | 12/1988 | Rosenberg . | |
| 5,062,849 | 11/1991 | Schelhas . | |
| 5,092,891 | 3/1992 | Kummer et al. | 623/16 |
| 5,098,433 | 3/1992 | Freedland | 606/60 |
| 5,217,462 | 6/1993 | Asnis et al. . | |
| 5,242,447 | 9/1993 | Borzone . | |
| 5,246,441 | 9/1993 | Ross et al. . | |
| 5,370,646 | 12/1994 | Reese et al. . | |

FOREIGN PATENT DOCUMENTS

| 0525352 A1 | 2/1993 | European Pat. Off. . |
|---|---|---|
| 1156667 | 5/1985 | Switzerland . |
| 1424823-A1 | 9/1988 | Switzerland . |

OTHER PUBLICATIONS

*Orthosorb® Absorbable Pin: Setting the Standard for Absorbable Internal Fixation for Shear or Torque Forces in the Foot, Hand, and Knee*, Product Information.

Primary Examiner—Michael Buiz
Assistant Examiner—Daphna Shaz
Attorney, Agent, or Firm—Knobbe, Martens, Olson & Bear, LLP

[57] ABSTRACT

Disclosed is a bone fixation device of the type useful for connecting two or more bone segments during the healing process. The device comprises an elongate pin having a distal anchor thereon. A proximal anchor is axially movably disposed with respect to the pin, to accommodate different bone dimensions and permit appropriate tensioning of the fixation device. The bone fixation device may comprise bioabsorbable or permanent materials such as poly-p-dioxanone, poly L-lactide (PLLA), nylon or stainless steel.

6 Claims, 5 Drawing Sheets

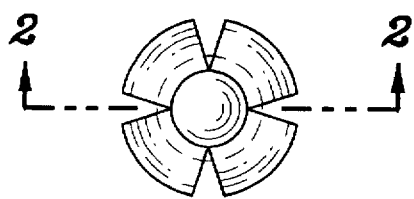
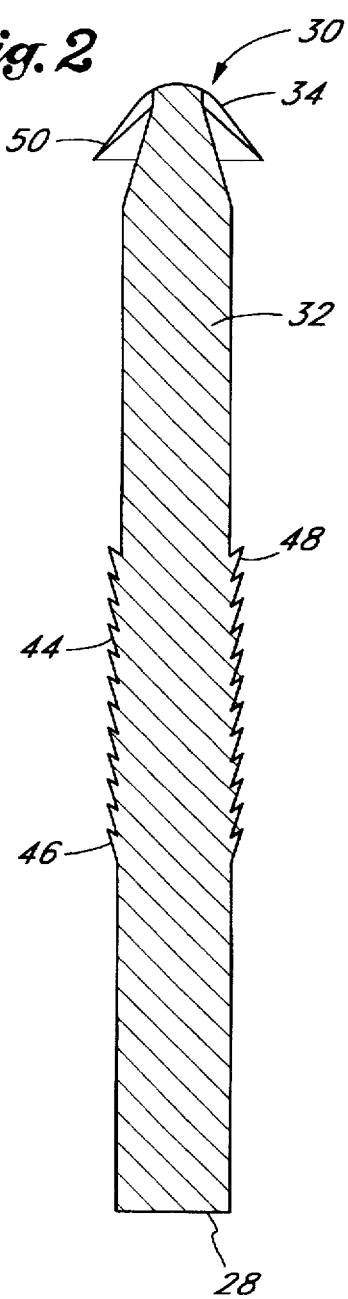
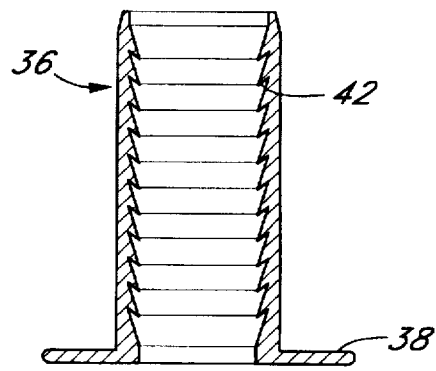
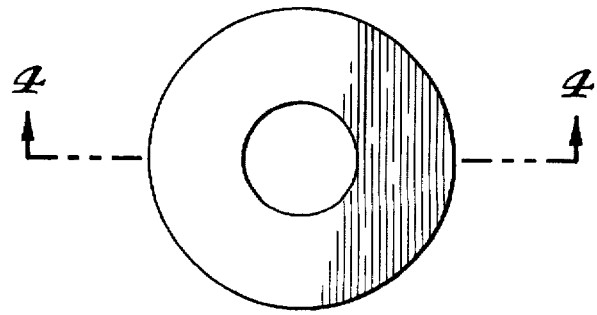

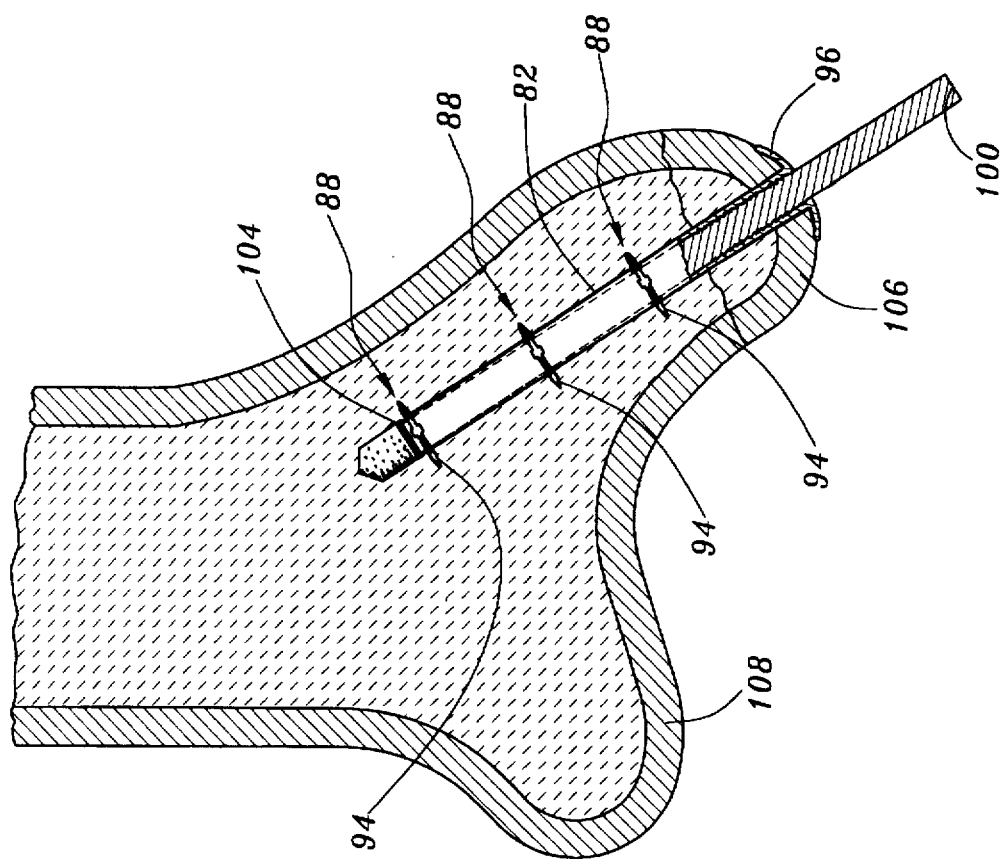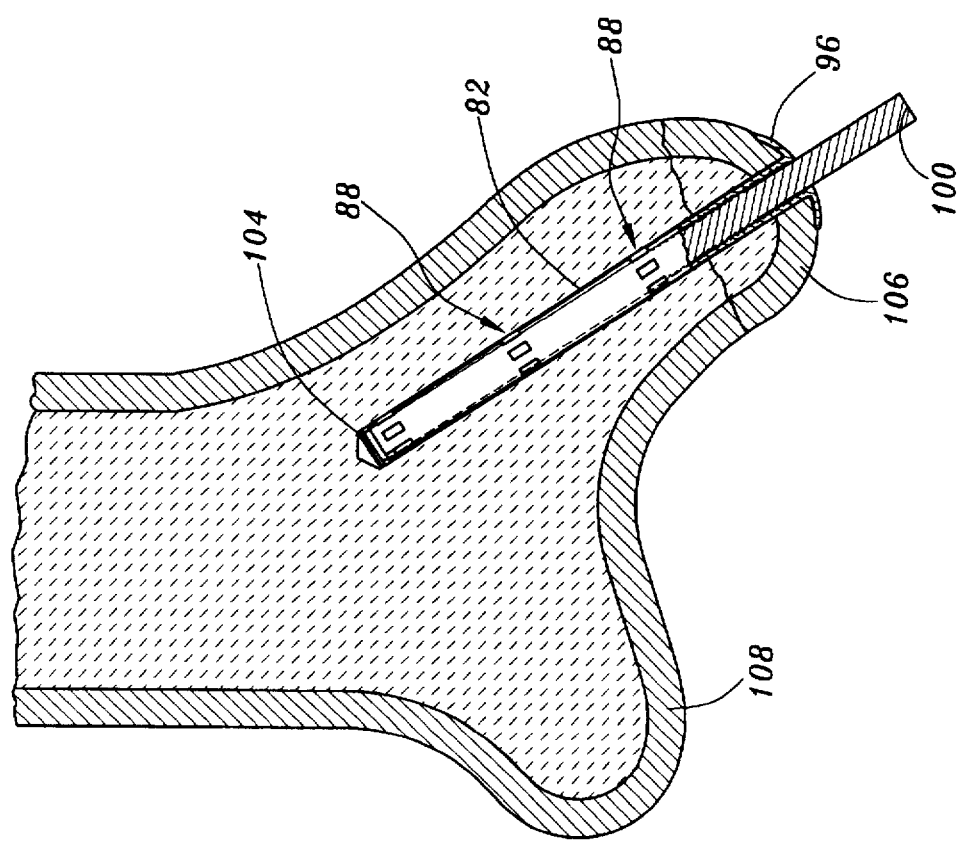

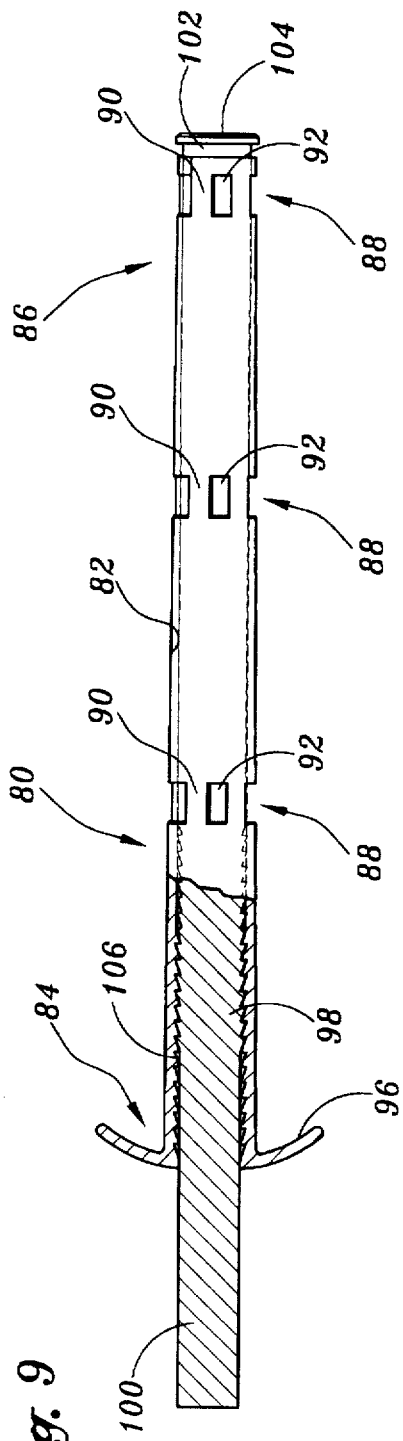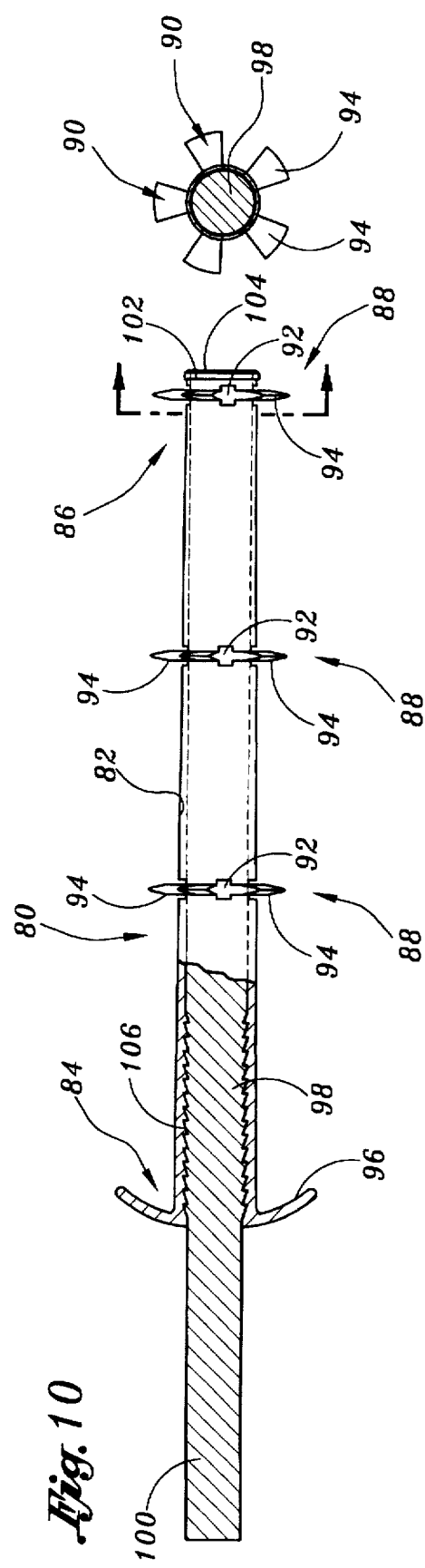

BONE FIXATION DEVICE

BACKGROUND OF THE INVENTION

The present invention relates to bone fixation devices and, more particularly, absorbable bone fixation pins of the type for securing two or more adjacent bone fragments together to provide shear-force stabilization during the healing period.

Bones which have been fractured, either by accident or severed by surgical procedure, must be kept together for lengthy periods of time in order to permit the recalcification and bonding of the severed parts. Accordingly, adjoining parts of a severed or fractured bone are typically clamped together or attached to one another by means of a pin or a screw driven through the rejoined parts. Movement of the pertinent part of the body may then be kept at a minimum, such as by application of a cast, brace, splint, or other conventional technique, in order to promote healing and avoid mechanical stresses that may cause the bone parts to separate during bodily activity.

The surgical procedure of attaching two or more parts of a bone with a pin-like device requires an incision into the tissue surrounding the bone and the drilling of a hole through the bone parts to be joined. Due to the significant variation in bone size, configuration, and load requirements, a wide variety of bone fixation devices have been developed in the prior art. In general, the current standard of care relies upon a variety of metal wires, screws, and clamps to stabilize the bone fragments during the healing process. Following a sufficient bone healing period of time, the percutaneous access site or other site must often be reopened to permit removal of the bone fixation device.

Long bone fractures are among the most common encountered in the human skeleton. Many of these fractures and those of other small bones and small bone fragments must be treated by internal and external fixation methods in order to achieve good anatomical position, early mobilization, and early and complete rehabilitation of the injured patient.

The internal fixation techniques commonly followed today frequently rely upon the use of Kirschner wires (K-wires), intramedullary pins, wiring, plates, screws, and combinations of the foregoing. The particular device or combination of devices is selected to achieve the best anatomic and functional condition of the traumatized bone with the simplest operative procedure and with a minimal use of foreign-implanted stabilizing material. A variety of alternate bone fixation devices is also known in the art, such as, for example, those disclosed in U.S. Pat. No. 4,688,561 to Reese, U.S. Pat. No. 4,790,304 to Rosenberg, and U.S. Pat. No. 5,370,646 to Reese, et al.

Notwithstanding the common use of the K-wire to achieve shear-force stabilization of bone fractures, K-wire fixation is attended by certain known risks. For example, a second surgical procedure is required to remove the device after healing is complete. Removal is recommended, because otherwise the bone under an implant becomes vulnerable to stress shielding as a result of the differences in the modulus of elasticity between metal and the bone.

In addition, a permanently implanted K-wire may provide a site for a variety of complications ranging from pin-tract infections to abscesses, resistant osteomyelitis, septic arthritis, and infected nonunion.

Another potential complication involving the use of K-wires is in vivo migration. Axial migration of K-wires has been reported to range from 0 mm to 20 mm, which can both increase the difficulty of pin removal as well as inflict trauma to adjacent tissue.

As conventionally utilized for bone injuries of the hand and foot, K-wires project through the skin. In addition to the undesirable appearance, percutaneously extending K-wires can be disrupted or cause damage to adjacent structures such as tendons if the K-wire comes into contact with external objects.

Notwithstanding the variety of bone fasteners that have been developed in the prior art, there remains a need for a bone fastener of the type that can accomplish shear-force stabilization with minimal trauma to the surrounding tissue both during installation and following bone healing.

SUMMARY OF THE INVENTION

There is provided in accordance with one aspect of the present invention a bone fixation device of the type useful for connecting two or more bone segments during the healing process. The device comprises an elongate pin body having proximal and distal ends, and a distal anchor on the distal end of the pin body. A proximal anchor is axially movably carried on the pin body.

An anchor retention structure on the pin body permits distal motion of the proximal anchor with respect to the pin body, but resists proximal motion of the proximal anchor with respect to the pin body. In one embodiment the retention structure comprises at least one ramped surface that inclines radially outwardly in the distal direction. Preferably, the bone fixation device comprises a bioabsorbable material, such as poly-p-dioxanone, poly-L-lactide or other materials.

In accordance with a further aspect of the present invention, there is provided a method of fixing two or more adjacent bone components with respect to each other. The method comprises the steps of drilling a hole through a first and a second adjacent bone component. A bone fixation device of the type having an elongate pin body, a distal anchor on a distal end of the pin body, and a proximal anchor axially movably supported by the pin body is provided. The bone fixation device is advanced distally through the hole until the distal anchor projects through the distal end of the hole. A proximal traction is applied to the pin body, while the proximal anchor is advanced distally along the pin body to apply a compressive force to the bone components. The compressive force is retained by resisting proximal movement of the proximal anchor with respect to the pin body. Preferably, the fixation device comprises a bioabsorbable material such as poly-p-dioxanone, so that the fixation device will be absorbed by the body, thereby eliminating the need for a post-healing removal step. Certain nonferrous materials may also have the advantage of sharing loads through healing bone, as compared to metals which spare loads and conduct energy much differently than the bone they are invested in. Load sharing may improve healing by allowing more normal bone physiology to occur around a fracture or osteotomy site.

Further features and advantages of the present invention will become apparent to those of skill in the art in view of the detailed description of preferred embodiments which follows, when considered together with the attached claims and drawings.

BRIEF DESCRIPTION OF THE DRAWINGS

FIG. 2 is a longitudinal cross-sectional view through the pin body of the present invention.

FIG. 3 is a distal end elevational view of the pin body of FIG. 2.

FIG. 4 is a longitudinal cross-sectional view of the proximal anchor of the bone fixation device.

FIG. 5 is a proximal end elevational view of the proximal anchor of the bone fixation device.

FIG. 7 is a cross-sectional schematic view of an alternate embodiment bone anchor of the present invention positioned within a bone.

FIG. 8 is a view of a bone anchor positioned within a bone as in FIG. 7, with the pin proximally withdrawn to set the anchors within the bone.

FIG. 9 is a partial cross-sectional side elevational view of the bone anchor of FIGS. 7 and 8.

FIG. 10 is a view of the bone anchor as in FIG. 9, with the pin proximally withdrawn to radially expand the bone anchors.

DETAILED DESCRIPTION OF PREFERRED EMBODIMENTS

Figure 1:
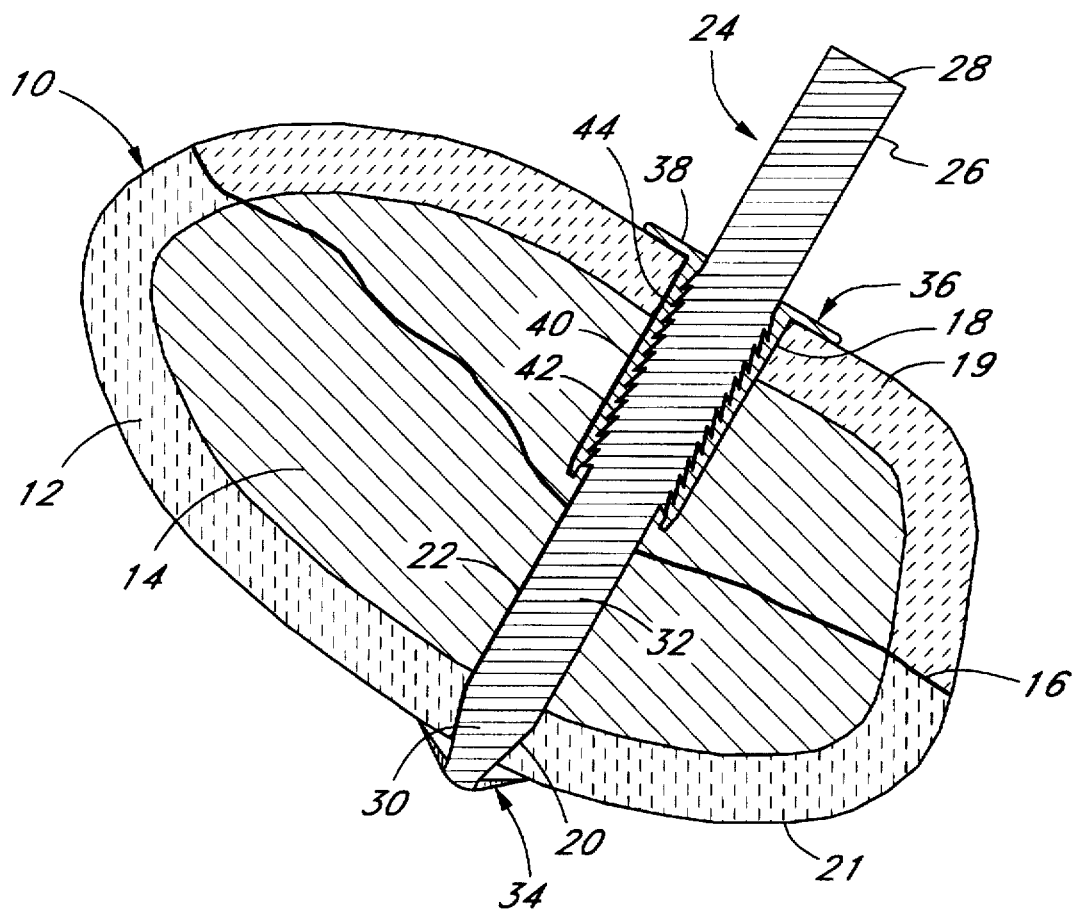
FIG. 1 is a cross-sectional schematic view of a bone fixation device of the present invention positioned within a fractured bone.

Although the application of the present invention will be disclosed in connection with the simplified bone fracture of FIG. 1, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer(s), all of which can be either permanent or absorbable.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. One example is the fixation of the medial malleolar avulsion fragment fixation with the radially and axially expanding compression device.

Referring to FIG. 1, there is illustrated generally a bone 10, shown in cross-section to reveal an outer cortical bone component 12 and an inner cancellus bone component 14. A fracture 16 is schematically illustrated as running through the bone 10 to divide the bone into what will for present purposes be considered a proximal component 19 and distal component 21. The fracture 16 is simplified for the purpose of illustrating the application of the present invention. However, as will be understood by those of skill in the art, the fracture 16 may extend through the bone at any of a wide variety of angles and depths. The bone fixation device of the present invention may be useful to stabilize two or more adjacent components of bone as long as each fracture may be traversed by the bone fixation device and anchored at opposing sides to provide a sufficient degree of stabilization.

A proximal aperture 18 is provided in the proximal component 19 of the bone 10, such as by drilling, as will be discussed. A distal aperture 20 is provided in an opposing portion of bone such as in distal bone component 21 and is connected to the proximal aperture 18 by way of a through hole 22, as is known in the art.

The bone fixation device 24 is illustrated in FIG. 1 in its installed position within the through hole 22. The bone fixation device 24 generally comprises an elongate pin 26 having a proximal end 28, a distal end 30, and an elongate pin body 32 extending therebetween.

The distal end 30 of pin 26 is provided with a distal anchor 34, as will be discussed. A proximal anchor 36 is also provided, such as a radially outwardly extending collar 38 connected to a tubular housing 40 adapted to coaxially receive the pin body 32 therethrough.

The radially interior surface of the tubular housing 40, in the illustrated embodiment, is provided with a plurality of retention structures 42. Retention structures 42 cooperate with corresponding retention structures 44 on the surface of pin body 32 to permit advancement of the proximal anchor 36 in the direction of the distal anchor 34 for properly sizing and tensioning the bone fixation device 24. Retention structures 42 then cooperate with retention structures 44 to provide a resistance to movement of the proximal anchor 36 in the proximal direction relative to pin body 32.

In use, the proximal projection of pin 26 which extends beyond the proximal anchor 36 after tensioning is preferably removed, such as by cutting, to minimize the projection of the bone fixation device 24 from the surface of the bone.

One embodiment of the pin 26, adapted for fixing oblique fractures of the fibula or metatarsal bone(s) is illustrated in FIG. 2. The bone fixation device 24 of this embodiment uses a generally cylindrical pin body 32. Although the present invention is disclosed as embodied in a pin body 32 having a generally circular cross section, cross sections such as oval, rectangular, or tapered to cause radial along with axial compression or others may also be used as desired for a particular application.

Pin body 32 has an axial length of within the range of from about 10 mm to about 70 mm in the as-manufactured condition. In one embodiment, the pin body 32 has an axial length of about 19 mm.

The retention structures 44 on the surface of pin body 32 in the illustrated embodiment comprise a plurality of annular ramp or ratchet-type structures which permit the proximal anchor 36 to be advanced in a distal direction with respect to pin body 32, but which resist proximal motion of proximal anchor 36 with respect to pin body 32. Although any of a variety of ratchet-type structures can be utilized in the present invention, the annular ramped rings illustrated in FIG. 2 are presently preferred in view of, among other advantages, the ability of the ratchet to function regardless of the rotational orientation of the proximal anchor 36 with respect to the pin body 32. In an embodiment having a noncircular cross section, or having a rotational link such as an axially-extending spline on the pin body 32 for cooperating with a complementary key on proximal anchor 36, the retention structures 42 can be provided on less than the entire circumference of the pin body as will be appreciated by those of skill in the art.

A single embodiment of the bone fixation device can be used for fixing fractures in bones having any of a variety of diameters. This is accomplished by providing the retention structures 44 over a predetermined axial length of the pin body 32. For example, in the illustrated embodiment, the retention structures 44 commence at a proximal limit 46 and extend axially until a distal limit 48. Axially extending the retention zone between limits 46 and 48 will extend the effective range of bone thicknesses which the pin 32 can accommodate. Although the retention structures 44 may alternatively be provided throughout the entire length of the pin body 32, retention structures 44 are not generally necessary in the most distal portions of pin body 32 in view of the minimum diameter of bones likely to be fixed.

In one embodiment of the invention, the distal limit 48 of retention structures 44 is spaced apart from the distal end 30 of pin body 32 by a distance within the range of from about 4 mm to about 8 mm, and, preferably, about 6 mm. The axial length of the portion of the pin body 32 having retention structures 44 thereon, from proximal limit 46 to distal limit 48, is generally within the range of from about 4 mm to about 8 mm, and, preferably, approximately 6 mm in an embodiment having a pin body length of about 19 mm.

Embodiments in accordance with the foregoing can be utilized to secure bones having an effective diameter within the range of from about 10 mm to about 18 mm. For the present purposes, the effective diameter is equivalent to the axial length of through hole 22. The fixation device 24 of the present invention can be readily adapted to fix bones having a greater effective diameter than the range recited above, by axially extending the proximal end 28 of the pin body 32 as desired, and by advancing the proximal limit 46 of the retention structures 44 in the proximal direction.

In general, the minimum diameter of the pin body 32 is a function of the construction material of the pin and the desired tensile strength for a given application. The maximum diameter is established generally by the desire to minimize the diameter of the through hole 22 while still preserving a sufficient structural integrity of the fixation device 24 for the intended application.

The diameter of pin body 32 will generally be in the range of from about 1.8 mm for small bones of the foot and hand to as large as 7.0 mm or larger for bones such as the tibia. In one embodiment of the invention intended for use in the first metatarsal, the pin 24 comprises poly-p-dioxanone and has a diameter of about 1.8 mm.

The distal anchor 34 in the illustrated embodiment comprises a plurality of ramped extensions 50 which incline radially outwardly in the proximal direction. Extensions 50 are compressible radially inwardly for the purpose of advancing the pin 32 through the through hole 22. Extensions 50 exert a radially outwardly directed bias so that they tend to extend radially outwardly from the pin body 32 once the distal anchor 34 has advanced out through the distal aperture 20 in bone 10. Proximal traction on the proximal end 28 of pin body 32 will thereafter tend to cause extensions 50 to seat firmly against the outside surface of distal bone component 21, as illustrated in FIG. 1. In one embodiment, the pin body 32 is provided with a central lumen extending axially therethrough (cannulated) for introduction over a guide pin as will be understood by those of skill in the art.

Although any of a variety of alternate designs for distal anchor 34 may be utilized in the context of the present invention, any such distal anchors 34 preferably permit axial distal motion of pin body 32 through the through hole 22, and thereafter resist proximal withdrawal of the pin body 32 from through hole 22. As will be appreciated by those of skill in the art, this feature allows the bone fixation device 24 to be set within a bone through a single proximal percutaneous puncture or incision, without the need to expose the distal component 21 or "backside" of the bone.

For a through hole having a diameter of about 2.3 mm, pin bodies 32 having an outside diameter of about 1.8 mm in the areas other than retention structures 44, and a maximum outside diameter of about 2.24 mm in the area of retention structures 44 have been found to be useful. In this embodiment, the maximum outside diameter of the distal anchor 34 was approximately 2.92 mm in the relaxed state. The axial length from the distal tip of distal end 30 to the proximal extent of extensions 50 was about 1.21 mm.

The pin body 32, together with the distal anchor 34 and other components of the present invention can be manufactured in accordance with any of a variety of techniques which are well known in the art, using any of a variety of medical-grade construction materials. For example, the pin body 32 and other components of the present invention can be injection-molded from a variety of medical-grade polymers including high density polyethylene, nylon and polypropylene. Distal anchor 34 can be separately formed from the pin body 32 and secured thereto in a post-molding operation, using any of a variety of securing techniques such as solvent bonding, thermal bonding, adhesives, interference fits and others known in the art. Preferably, however, the distal anchor 34 is integrally molded with the pin body 32.

Retention structures 44 can also be integrally molded with the pin body 32. Alternatively, retention structures 44 can be machined or pressed into the pin body 32 in a post-molding operation, or secured using other techniques depending upon the particular design.

In a preferred embodiment, the components of the bone fixation device 24 are injection-molded from a bioabsorbable material, to eliminate the need for a post-healing removal step. One suitable bioabsorbable material which appears to exhibit sufficient structural integrity for the purpose of the present invention is poly-p-dioxanone, such as that available from the Ethicon Division of Johnson & Johnson. Poly-L-lactide may alternatively be used.

The pin body 32 cooperates with a proximal anchor 36 to accomplish the fixation function of the present invention. Proximal anchor 36 is preferably axially movably carried by the pin body 32 throughout a sufficient axial range of motion to accommodate a variety of bone diameters.

In the embodiment illustrated in FIG. 4, the proximal anchor 36 comprises a collar 38 for contacting the proximal bone component 19. Collar 38 preferably comprises a radially-outwardly extending annular flange to optimize contact with the proximal bone component 19. Alternatively, proximal collar 38 may comprise one or more radially-outwardly extending stops, a frusto-conical plug, or other structures which stop the distal progress of proximal anchor 36 with respect to the through hole 22.

Collar 38 is axially movably disposed with respect to pin body 32 such as by connection to a tubular housing 40. Tubular housing 40 is concentrically positioned on pin body 32, and is provided on its interior surface with at least one, and preferably a plurality, of retention structures 42. Retention structures 42 are configured to cooperate with the complementary retention structures 44 on the pin body 32 to permit axial distal advancement of collar 38 with respect to pin body 32, but resist proximal motion of collar 38 with respect to pin body 32, as has been discussed.

In a preferred embodiment of the present invention, the minimum interior diameter of the tubular housing 40 is about 2.00 mm. The maximum interior diameter of the tubular housing 40, at the radial outwardmost bottom of the annular recesses adapted to cooperate with annular ridges 44 on pin body 32, is about 2.17 mm. The outside diameter of the collar 38 is about 2.70 mm, and the thickness in the axial direction of annular collar 38 is about 0.20 mm. The proximal anchor 36 can be readily constructed using other dimensions and configurations while still accomplishing the desired function, as will be apparent to those of skill in the art in view of the disclosure herein.

In use, a bone is first identified having a fracture which is fixable by a pin-type fixation device. The clinician assesses the bone, selects a bone drill and drills a through hole 22 in accordance with conventional techniques.

A bone fixation device 24 having an axial length and outside diameter suitable for the through hole 22 is selected. The distal end 30 of the bone fixation device 24 is percutaneously advanced towards the bone, and subsequently advanced through the through hole 22 until distal anchor 34 exits the distal aperture 20. The proximal anchor 36 may be positioned on the bone fixation device 24 prior to positioning of the pin body 32 in the through hole 22, or following placement of the pin body 32 within through hole 22.

Proximal traction is applied to the proximal end 28 of pin body 32, to seat the distal anchor 34. While proximal traction is applied to the proximal end 28 of pin body 32, such as by conventional hemostats or a calibrated loading device, the proximal anchor 36 is advanced distally until the anchor 36 fits snugly against the proximal component 19 of the bone. Appropriate tensioning of the bone fixation device 24 is accomplished by tactile feedback or through the use of a calibration device for applying a predetermined load on implantation.

Following appropriate tensioning of the proximal anchor 36, the proximal end 28 of the pin body 32 is preferably cut off and removed. Pin body 32 may be cut using conventional bone forceps which are routinely available in the clinical setting.

Following trimming the proximal end 28 of pin 26, the access site may be closed and dressed in accordance with conventional wound closure techniques.

Preferably, the clinician will have access to an array of bone fixation devices 24, having different diameters and axial lengths. Upon encountering a bone for which the use of a fixation device is deemed appropriate, the clinician will assess the dimensions and load requirements of the bone, and select a bone fixation device from the array which meets the desired specifications.

Figure 6:
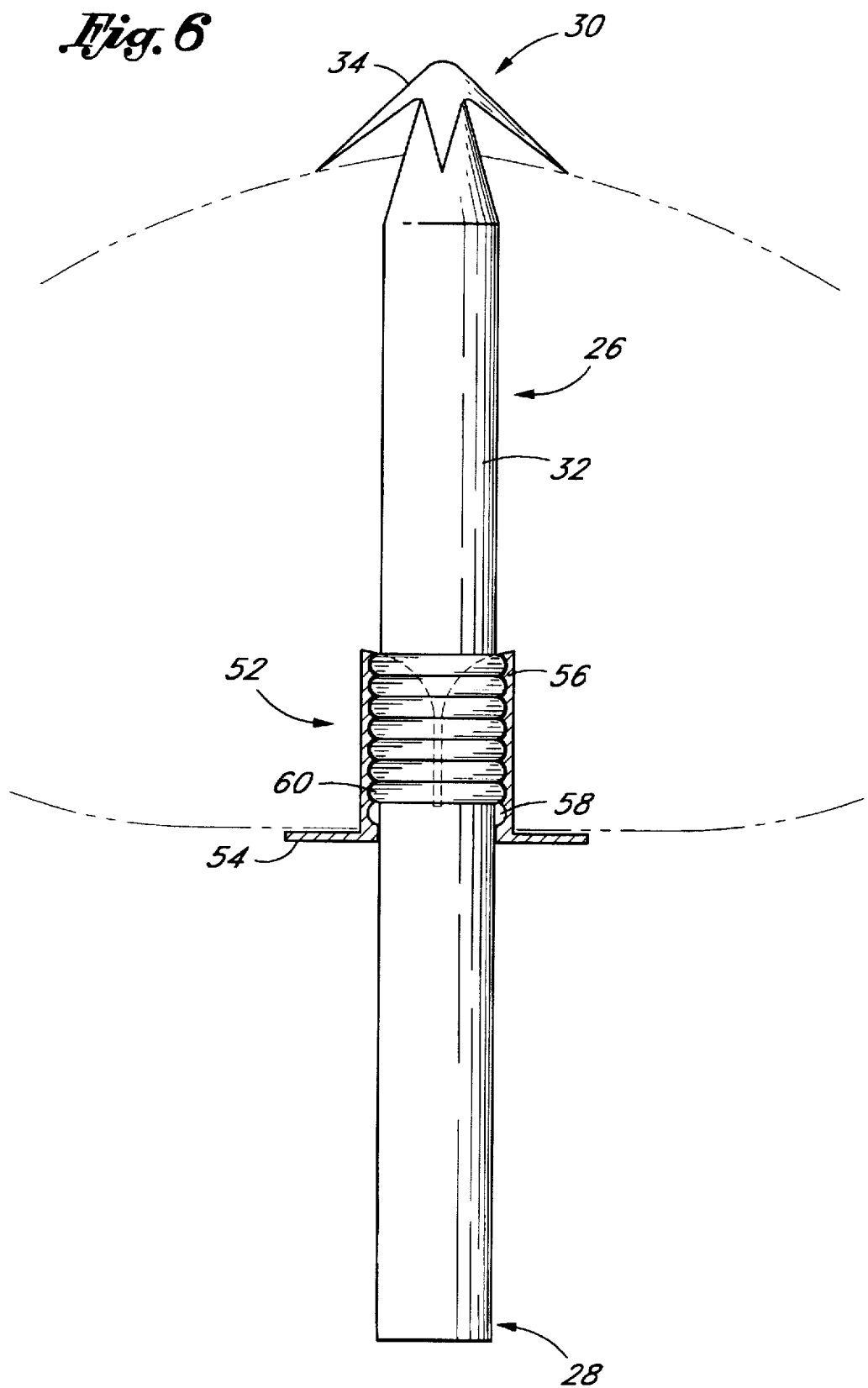
FIG. 6 is a side elevational view of an alternate embodiment of the bone fixation device of the present invention.

Referring to FIG. 6, there is disclosed an alternate embodiment of the fixation pin. The fixation pin 26 illustrated in FIG. 6 is identical to the embodiments previously discussed, except with respect to the proximal anchor 52. Proximal anchor 52 comprises a radially outwardly extending annular collar 54 or other structure for resisting motion of the proximal anchor 52 in a distal direction through the aperture in the bone. Collar 54 is connected to a proximal portion of the tubular housing 56, analogous to housing 40 previously discussed. Tubular housing 56 is adapted to receive the pin body 32 therethrough.

The radially inwardly facing surface of tubular housing 56 is provided with a plurality of retention structures 58. In this embodiment, retention structures 58 comprise a plurality of recesses or grooves which extend radially outwardly into the tubular housing 56. Retention structures 58 are adapted to cooperate with corresponding retention structure 60 secured to or integral with the pin 32. Retention structure 60 in this embodiment comprise a plurality of radially outwardly extending annular rings or threads, which are adapted to be received within the corresponding retention structures 58. In this embodiment, the proximal anchor 52 is unable to move in an axial direction with respect to pin 32 unless sufficient axial force is applied to plastically-deform the retention structures 58 and/or retention structures 60 so that the tubular housing 56 snaps, ridge by ridge, in the direction of the axial force. The precise amount of axial force necessary to overcome the resistance to motion of proximal anchor 52 with respect to pin 32 can be optimized through appropriate tolerancing of the corresponding retention structures, together with the selection of materials for the proximal anchor 52 and/or pin 32. Preferably, the tolerances and construction details of the corresponding retention structures 58 and 60 are optimized so that the proximal anchor 52 may be advanced distally over the pin 32 using manual force or an installation tool, and the proximal anchor 52 will have a sufficient retention force to resist movement of the bone fragments under anticipated use conditions.

For any of the embodiments disclosed herein, installation can be simplified through the use of a one-hand installation tool. Preferably, the installation tool comprises a piston grip or plier-type grip so that the clinician can position the tool at the proximal extension of pin 32 and through one or more contractions with the hand, the proximal anchor 52 and distal anchor 34 can be drawn together to appropriately tension against the bone fragments. The use of a precalibrated tool can permit the application of a predetermined tension in a uniform manner from pin to pin.

Calibration of the installation device to set a predetermined load on the pin can be accomplished through any of a variety of means which will be understood to those of skill in the art. For example, the pin 32 may be provided with one or more score lines or other modifications which limit the tensile strength of the part at one or more predetermined locations. In this manner, axial tension applied to the proximal end 28 with respect to the collar 54 will apply a predetermined load to the bone before the pin 32 will separate at the score line. Alternatively, internal structures within the installation tool can be provided to apply tension up to a predetermined limit and then release tension from the distal end of the tool.

Referring to FIGS. 7 through 10, there is disclosed an alternate embodiment of the fixation pin of the present invention. In previous embodiments, the fixation pin was adapted for use in a through hole, which exited the backside of the bone. In some bones, and some types of fractures, however, the need for the pin to exit the rear surface of the bone may be disadvantageous. In these applications, the pin is preferably configured to anchor inside of the bone without the need to exist the rear surface. This is the case, for example, in the Malleolar fixation illustrated in FIGS. 7 and 8, in which a bone fragment 106 is fixed to the bone 108.

The fixation device illustrated in FIGS. 9 and 10 comprises generally a fastener and pin assembly 80. The assembly 80 comprises a tubular sleeve 82 having a proximal end 84 and a distal end 86. Near the distal end 86 and preferably also at one or more additional positions along the tubular sleeve 82, the tubular sleeve 82 is provided with one or more anchors 88.

In the illustrated embodiment, the anchor 88 comprises a plurality of axially-extending strips 90 spaced apart circumferentially around the tubular sleeve 82. Each two adjacent axially-extending strips 90 is separated by a space 92. Space 92 may take the form of an axially and circumferentially-extending window, or an axially-extending slit as will be apparent to those of skill in the art.

The anchor 88 is designed such that as the axial length of the tubular sleeve 82 is shortened such as by axial compression, each axially-extending strip 90 is forced to fold radially outwardly as illustrated to provide an interference surface 94. Interference surface 94 is adapted to engage cancellous bone material to resist axial proximal withdrawal of the tubular sleeve 82 from the bone.

The anchor 88 may comprise two or more axially-extending strips 90, and, in one embodiment, comprises three axially-extending strips 90. Four or five or more axially-extending strips 90 may also be utilized for each anchor 88. Preferably, the axially-extending strips 90 are evenly circumferentially spaced around the tubular sleeve 82, to provide a radially symmetrical distribution of proximal force to the cancellous bone.

The total number of anchors 88, as well as the total surface area of the interference surfaces 94 can be varied to optimize the anchor retention force for each given application of the fastener and pin assembly 80.

The sleeve is preferably also provided with a proximal stop such as a proximal flange 96 which extends radially outwardly from the sleeve 82. Preferably, the flange 96 is slightly concave in the distal direction to provide a complimentary fit with the bone surface, and/or a spring effect with deformation.

Depending upon the construction of the tubular sleeve 82 and geometry of the strips 90, the point along strip 90 where bending occurs may vary. To facilitate reproducible bending of strip 90 and the creation of predictable interference surfaces 94, the strip 90 can be provided with one or more circumferentially extending grooves or other modifications which will preferentially bend under axial compression. For example, circumferential grooves can be located at the proximal end and distal end of each strip 90. An additional groove may also be desirable mid way between the proximal and distal ends.

The tubular sleeve 82 can be constructed in any of a variety of ways known in the art. For example, it can be injection molded in its final configuration. Alternatively, windows 92 can be cut into previously formed tube stock. Construction materials described elsewhere herein can be used for the present embodiment. The present embodiment can also be constructed generally in accordance with the dimensions discussed in connection with previous embodiments, or may be varied to suit the particular intended application. For applications such as that illustrated in FIGS. 7 and 8, for example, fastener and pin assembly 80 will generally be provided with an axial length on the order of from about 40 mm to about 70 mm.

The fastener and pin assembly 80 further comprises an axially-extending pin 98, which is axially movably disposed within the tubular sleeve 82. Pin 98 comprises a proximal end 100 and a distal end 102. The distal end 102 is axially interlocked with the distal end 86 of the tubular sleeve 82. In the illustrated embodiment, distal end 102 of pin 98 is provided with a stop 104 such as a radially outwardly extending annular flange or cap having a diameter greater than the inside diameter of the tubular sleeve 82. In this manner, proximal displacement of the pin 98 within tubular sleeve 82 imparts an axially-compressive force on the tubular sleeve 82. Any of a variety of interference fit structures for providing a stop surface 104 can be utilized, as will be apparent to those of skill in the art in view of the disclosure herein.

The interior surface of the tubular sleeve 82 and outer surface of the pin 98 are provided with complimentary retention structures 106, such as any of those described previously herein, for permitting the pin 98 to be withdrawn proximally with respect to the proximal end of tubular sleeve 82, but to resist distal motion of the pin 98 with respect to tubular sleeve 82.

As will be apparent in view of FIG. 7 and the discussion above, proximal withdrawal of the proximal pin end 100 with respect to the proximal flange 96 will cause the anchor 88 to collapse thereby forcing interference surfaces 94 to incline radially outwardly from the tubular sleeve 82 to engage cancellous bone while the bone fragment 106 is held against the bone 108. Following withdrawal of proximal pin end 100 to the desired tension, the proximal pin end 100 projecting beyond flange 96 may be severed as has been previously discussed.

In a preferred embodiment of the invention, at least a portion of the pin 98 is provided with an outside diameter which tapers from a relatively larger diameter near the distal end 102 towards a relatively smaller diameter at the proximal end 100. The tubular sleeve 82 may be provided with a corresponding taper of its inside diameter from a relative large inside diameter at the distal end 86 to a relatively smaller inside diameter at the proximal end 84. Preferably, the outside diameter of the tubular sleeve 82 remains substantially constant throughout. In this embodiment, proximal withdrawal of the pin 98 will cause a radial expansion of the tubular sleeve 82 to assist in retention of the tubular sleeve 82 within a bore in the bone.

Preferably, the corresponding tapered surfaces on the pin 98 and sleeve 82 are relatively dimensioned such that (disregarding the retention structures 106 for present purposes) the proximal end 100 of pin 98 can be inserted into the distal end 86 of sleeve 82 and the pin 98 can be freely advanced proximally into the sleeve 82 for an axial distance before the corresponding tapered surfaces engage. The corresponding tapered surfaces engage at a point where the axial compression on the tubular sleeve has already caused anchor(s) 88 to deform. Further proximal axial motion of pin 98 within sleeve 82 will radially expand the sleeve 82 while the radial expansion of anchor(s) simultaneously continues.

In use, the bone fragment 106 is held in position against bone 108 and a hole is drilled using conventional bone drilling techniques. The fastener and pin assembly 80 is then advanced into the hole, preferably over a guiding wire until proximal flange 96 is seated against the bone fragment 106. Proximal withdrawal of pin 98 with respect to flange 96 first causes axial compression and resulting radial expansion of anchor 88. Further proximal withdrawal of pin 98 thereafter simultaneously causes radial expansion of at least a portion of tubular sleeve 82. The appropriate pulling tension on pin 98 may then be applied to set retention structures 106 as desired.

The pin 98 is optionally provided with an axially-extending central lumen (not illustrated) for axially-slidably receiving an alignment pin therethrough. This allows the use of a self-tapping and drilling alignment pin (not illustrated), which can be drilled into the appropriate bone site as is known in the art. The fastener and pin assembly 80 may thereafter be advanced over the proximal end of the pin and advanced distally along the pin until it is seated appropriately within the bone.

In one embodiment of the invention the overall length of the pin was about 70 mm and the overall length of the sleeve was about 55 mm in the uncompressed configuration. When compressed, the sleeve had a length of about 48 mm. The outside diameter of the sleeve was about 6.5 mm. The thickness of the proximal flange was about 1.3 mm, and the diameter of the proximal flange was about 15 mm. The diameter through the radially expanded anchors was about 11.0 mm.

The specific dimensions of any of the bone fixation devices of the present invention can be readily varied depending upon the intended application, as will be apparent to those of skill in the art in view of the disclosure herein. In addition, although the first principle embodiment of the present invention was disclosed in the context of a cortical to cortical compression fixation which uses a through hole, and a second principle embodiment of the invention was disclosed in terms of a non-through hole application, either device may be readily dimensioned to suit the other application. For example, the embodiments of FIGS. 7 through 10 can readily be utilized in a through hole fixation of the type illustrated in FIG. 1, with the distal most anchor 80 engaging the rear cortical surface and the proximal flange 96 engaging the proximal cortical surface. Intermediate anchors 88 such as are illustrated in FIGS. 7 through 10 may or may not be included in a through hole embodiment of the invention.

Although the present invention has been described in terms of certain preferred embodiments, other embodiments of the invention including variations in dimensions, configuration and materials will be apparent to those of skill in the art in view of the disclosure herein. Accordingly, the present invention is intended to be described solely by reference to the appended claims, and not limited to the preferred embodiments disclosed herein.

What is claimed is:

1. A bone fixation device, comprising:

an elongate pin body having proximal and distal ends;

a distal anchor on the pin body, said distal anchor moveable between a reduced cross-sectional area for implantation of the device and an enlarged cross-sectional area for anchoring the device, said distal anchor biased in the direction of the enlarged cross-sectional area;

a proximal anchor, axially movably carried by the pin body, said proximal anchor comprising a tubular housing coaxially disposed about the pin body;

said tubular housing comprising at least one radially inwardly facing surface structure which cooperates with a ramped surface on the pin body to permit distal travel of the proximal anchor with respect to the pin body but which resists proximal travel of the proximal anchor with respect to the pin body;

an anchor retention structure on the pin body for permitting distal motion of the proximal anchor with respect to the pin body but resisting proximal motion of the proximal anchor relative to the pin body, said retention structure comprising at least one ramped surface that inclines radially outwardly in the distal direction.

2. A bone fixation device as in claim 1, wherein said fixation device comprises poly-p-dioxanone, PGA, PLLA or other bio-absorbable or biologically incorporated substance.

3. A bone fixation device as in claim 1, said housing having a radially-outwardly directed annular flange on the proximal end thereof.

4. A bone fixation device as in claim 1, wherein the distal anchor is radially enlargeable from a first, reduced diameter for passing through an aperture in a bone in a distal direction, and a second, relatively larger diameter for resisting movement of the distal anchor in a proximal direction through the aperture in the bone.

5. A bone fixation device as in claim 4, wherein the distal anchor is biased towards the larger diameter.

6. A method of fixing two or more adjacent bone components with respect to each other, comprising the steps of:

drilling a hole through a first and a second adjacent bone components;

providing a bone fixation device of the type having an elongate pin body, a distal anchor on the pin body, and a proximal anchor axially movably supported by the pin body, said distal anchor moveable from an insertion orientation to an anchoring orientation and biased in the direction of the anchoring orientation;

advancing the bone fixation device through the hole with the distal anchor restrained in the insertion orientation until the distal anchor projects through the distal end of the hole;

permitting the bias to automatically move the distal anchor from the insertion orientation to the locking orientation;

applying a proximal traction on the pin body;

advancing the proximal anchor distally along the pin body to apply a compressive force to the bone components; and retaining the compressive force by an anchor retention structure that permits distal travel of the proximal anchor but resists proximal movement of the proximal anchor with respect to the pin body.

* * * * *